United States Patent [19]

Manara et al.

[11] Patent Number: 5,002,946

[45] Date of Patent: Mar. 26, 1991

[54] PHENYLETHANOLAMINE ANALOG ACTIVE COMPOUNDS FOR THE TREATMENT OF GASTROINTESTINAL DISEASES

[75] Inventors: Luciano Manara, Alessandria; Tiziano Croci; Alberto Bianchetti, both of Milan, all of Italy

[73] Assignee: Sanofi, Paris, France

[21] Appl. No.: 501,302

[22] Filed: Mar. 23, 1990

Related U.S. Application Data

[63] Continuation of Ser. No. 65,848, Jun. 24, 1987, abandoned.

[30] Foreign Application Priority Data

Jun. 27, 1986 [IT] Italy .................... 20924A/86

[51] Int. Cl.$^5$ ............... A61K 31/535; A61K 31/445; A61K 31/425; A61K 31/40; A61K 31/34; A61K 31/195; A61K 31/24; A61K 31/165; A61K 31/135

[52] U.S. Cl. ....................... 514/230.8; 514/231.8; 514/232.2; 514/236.8; 514/316; 514/326; 514/330; 514/331; 514/374; 514/423; 514/469; 514/539; 514/567; 514/620; 514/649; 514/651; 514/653; 514/654

[58] Field of Search ............... 514/227, 230.8, 231.8, 514/232.2, 236.8, 316, 326, 330, 331, 374, 423, 469, 539, 567, 620, 649, 651, 653, 654

[56] References Cited

FOREIGN PATENT DOCUMENTS 0007204 1/1980 European Pat. Off. .
0007205 1/1980 European Pat. Off. .
0023385 1/1980 European Pat. Off. .
0164700 12/1985 European Pat. Off. .

OTHER PUBLICATIONS

European Journal of Pharmacology, "The Rat Lipolytic beta-Adrenoceptor: studies using . . . " 1984, vol. 100 pp. 309-319.
Nature "Atypical beta-adrenoceptor on brown adipocytes as target for anit-obesity drugs," 1984, vol. 309 pp. 163-165.
Life Science, "Stimulation of cyclic AMP and lipolysis in adipose tissue of normal . . . " 1983, vol. 32 pp. 1515-1522.
International Journal of Obesity, "Thermogensesis and weight control," 1984, vol. 8 pp. 65-78.
Diabetologia, "Anti-diabetic activity of Ro 16-8714; a beta-adrenergic against . . . ," 1984, vol. 27, p. 291A.
Fed. Proc., "Antiobesity activity of Ro 16-8714 in diet-induced obese (DIO) rats," S. Hogan et al., vol. 44, No. 4.
Goodman and Gilman's: The Pharmacological basis of therapeutics, 1985 pp. 145-150, chapter 8 Macmillan Publ. Co.
Recueil Trav. Chim. Paysbas, "synthesis of Beta--Phinylethylamine Derivatives . . . ," 1973, vol. 92, pp. 1281-1291.
Bristow et al., "Analysis of Beta Receptor Drug Interactions in Isolated Rabbitt Atrium . . . ", J. Pharmacol. Exp. Ther., 1970, vol. 171; pp. 56-61.
Daniel, "Pharmacology of Adrenergic, Cholinergic and Drugs Acting on Other Receptors . . . ", Handbook of Exp. Pharmacol. 1982, vol. 59/II, pp. 262-263.
Coleman et al., "β-Adrenoceptors in Guinea-pig Gastric Fundus . . . ", Br. J. Pharmacol., Proc. Supplement, 1987, vol. 90, page 40P.
Bond et al., "A Response to Isoprenaline . . . ", Br. J. Pharmacol., 1987, vol. 91, pp. 683-686.

Primary Examiner—Stanley J. Friedman
Assistant Examiner—Raymond J. Henley, III
Attorney, Agent, or Firm—Foley & Lardner

[57] ABSTRACT

Phenylethanolamine analog active compounds, optionally substituted on the phenyl group with an halogen atom or with an alkyl or trifluoromethyl group and substituted on the amino group with a phenylalkyl or phenoxy alkyl group optionally substituted on the benzene ring, are used for the treatment and/or prophylaxis of gastrointestinal diseases associated with a smooth muscle contraction.

21 Claims, No Drawings

PHENYLETHANOLAMINE ANALOG ACTIVE COMPOUNDS FOR THE TREATMENT OF GASTROINTESTINAL DISEASES

This application is a continuation, of application Ser. No. 07/065,848, filed June 24, 1987 now abandoned.

The present invention relates to the use of certain phenylethanolamine derivatives and of their pharmaceutically acceptable salts in a method for the prophylaxis and/or treatment of gastrointestinal diseases associated with a smooth muscle contraction without any relevant cardiac effects.

European published patent application Nos. 6735, 7204, 21636, 23385, 25331, 28105, 40000, 40915, 52963, 61907, 63004, 66351, 68669, 70133, 70134, 89154, 91749, 95827, 99707, 101069, 140359, 146392, 164700, 170121, 170135, 171519, Belgian patent 900.983, United Kingdom patent specification 2133986, Australian published patent application 84/31944, International published patent application WO 84/00956 and U.S. Pat. No. 4,391,826 describe phenylethanolamines, optionally modified in order to form ethers, esters or cyclic derivatives, having antihyperglycaemic and/or antiobesity activity.

It has now been found that the phenylethanolamines, their derivatives or analogs, as well as their salts, described in the above mentioned patents, may be used for the preparation of pharmaceutical compositions acting on the gastrointestinal smooth muscle useful for the treatment of diseases associated with a smooth muscle contraction without any relevant side effects on heart or on the respiratory apparatus, provided that said products do not bear any hydroxy group on the benzene ring of phenylethanolamine.

So, the present invention relates to a method for the treatment and/or prophylaxis of gastrointestinal diseases associated with a smooth muscle contraction in mammals which comprises administering to said mammals in need of such treatment and/or prophylaxis an effective and/or prophylactic amount of a phenylethanolamine analog active compound having the formula

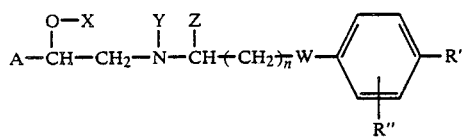

wherein:
n is 1, 2 or 3;
A is a benzofuran-2-yl group or a phenyl group unsubstituted or substituted with one or two halogen atoms, a lower alkyl or a trifluoromethyl group;
R' is . hydrogen;
. a lower alkyl group;
. a functional group selected from the group consisting of: hydroxy; lower alkoxy; lower alkenyloxy; lower alkynyloxy; cycloalkyloxy; lower cycloalkyl-alkoxy; benzyloxy; phenoxy; mercapto; (lower alkyl)thio; (lower alkenyl)thio; (lower alkynyl)thio; cycloalkylthio; (cycloalkyl-lower alkyl)thio; benzylthio; phenylthio; (lower alkyl)sulfinyl; (lower alkenyl)sulfinyl; (lower alkynyl)sulfinyl; cycloalkylsulfinyl; (cycloalkyl-lower alkyl)sulfinyl; benzylsulfinyl; phenylsulfinyl; (lower alkyl)sulfonyl; (lower alkenyl)sulfonyl; (lower alkynyl)sulfonyl; cycloalkylsulfonyl; (cycloalkyl-lower alkyl)sulfonyl; benzylsulfonyl; phenylsulfonyl; cyano; nitro; amino unsubstituted or substituted with one or two identical or different radicals selected from the group consisting of lower alkyl, lower alkenyl, lower alkynyl, cycloalkyl, cycloalkyl-lower alkyl, benzyl, phenyl; carboxy; lower carbalkoxy; (lower alkenyloxy)carbonyl; (lower alkynyloxy)carbonyl; cycloalkyloxycarbonyl; (cycloalkyl-lower alkoxy)carbonyl; benzyloxycarbonyl; phenoxycarbonyl; carbamoyl unsubstituted or substituted on the amino group with one or two identical or different radicals selected from the group consisting of lower alkyl, lower alkenyl, lower alkynyl, cycloalkyl, cycloalkyl-lower alkyl, benzyl, phenyl; a R radical selected from the group consisting of a lower alkyl group substituted with a functional group, a lower alkenyl group substituted with a functional group, a lower alkynyl group substituted with a functional group, a (lower alkyl)phenyl group substituted on the benzene ring with a lower alkyl or a functional group, a (lower alkenyl)phenyl group substituted on the benzene ring with a lower alkyl or a functional group, a (lower alkynyl)phenyl group substituted on the benzene ring with a lower alkyl or a functional group, a benzyl group substituted on the benzene ring with a lower alkyl or a functional group, or a phenyl group unsubstituted or substituted with a lower alkyl or a functional group, the functional group being as defined hereinabove;
. an O-R group, wherein R is as defined hereinabove;
. a S-R group, wherein R is as defined hereinabove;
. a SO-R group, wherein R is as defined hereinabove;
. a SO$_2$-R group, wherein R is as defined hereinabove;
. a NRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine;
. a COOR group, wherein R is as defined hereinabove;
. a CO-SR group, wherein R is as defined hereinabove;
. a CONRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine;
. a SO$_2$NRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine;
R" represents
. hydrogen;
. a halogen;
. a lower alkyl;
. a functional group as defined hereinabove;
. a O-R group, wherein R is as defined hereinabove;
. a COOR group, wherein R is as defined hereinabove;
. a CONRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine;
W represents a direct bond or an oxygen atom;

X represents hydrogen, a lower alkyl or a lower alkanoyl;

Y represents hydrogen or a A'—CH(OH)—CH$_2$— group, wherein A' is identical to A, but other than benzofuran-2-yl; or X and Y, together, form a methylene group, unsubstituted or substituted with a lower carbalkoxy group, an ethylene group, unsubstituted or substituted with an oxo group, or a 1,3-propylene group; and Z represents hydrogen or a lower alkyl; or of a pharmaceutically acceptable salt thereof.

The terms "lower alkyl", "lower alkenyl" and "lower alkynyl", as used herein, designate monovalent radicals deriving from aliphatic hydrocarbons saturated or containing a double or a triple bond and having from 1 to 6 carbon atoms, such as methyl, ethyl, propyl, isopropyl, t-butyl, neopentyl, allyl, crotyl, propargyl.

The term "cycloalkyl" designates a monovalent radical of an alicyclic hydrocarbon containing from 3 to 8 carbon atoms, preferably cyclopropyl, cyclopentyl and cyclohexyl.

The terms "lower alkoxy", "lower alkenyloxy", "lower alkynyloxy", "cycloalkyloxy" and the corresponding thio derivatives, as used herein, designate the group hydroxy or thiol etherified with a lower alkyl, a lower alkenyl, a lower alkynyl or with a cycloalkyl, as defined hereinabove.

The term "lower carbalkoxy" designates a lower alkyl ester of the carboxy group, wherein the lower alkyl is as defined hereinabove; more particularly, the terms "carbalkoxy", "carbomethoxy" and "carbethoxy" are used here as synonyms of the terms alkoxycarbonyl, methoxycarbonyl and ethoxycarbonyl.

The term "lower alcanoyl" designates a carbonyl group substituted with a lower alkyl as defined hereinabove.

The term "halogen" designates the four common halogens, i.e. fluorine, chlorine, bromine and iodine, among which fluorine and, more particularly, chlorine are preferred.

The compounds of formula I may be in an optical inactive form or in an optical active form selected among the enantiomers, the diastereoisomers and their mixtures. All these compounds and their pharmaceutically acceptable salts may be used according to the present invention.

The pharmaceutically acceptable salts of the compounds of formula I, for example hydrochloride, hydrobromide, sulfate, hydrogen sulfate, dihydrogen phosphate methanesulfonate, methylsulfate, oxalate, maleate, fumarate, naphthalene-2-sulfonate, are those which are obtained by treating the free base, dissolved for example in an alcohol such as isopropanol, with a solution of the selected acid in the same solvent.

When the compound of formula I has a free carboxy group, its amphoteric character allows the preparation of salts with both acids and bases. The pharmaceutically acceptable salts with bases are preferably those prepared with alkali metals such as sodium, but the salts prepared with organic bases, such as the salt with tromethamine, are also suitable.

Preferred compounds of formula I, are the compounds in which:

n is 1 or 2;

A is phenyl, 2-fluorophenyl, 3-chlorophenyl or 3-trifluoromethylphenyl group;

R' is . a functional group selected from the group consisting of hydroxy, lower carbalkoxy, carboxy, carbamoyl; or . an O-R group, wherein R is a lower alkyl group or a lower alkenyl substituted with a functional group selected from lower carbalkoxy and carboxy;

R" and X are both hydrogen;

W is a direct bond;

Y is hydrogen or a A'—CH(OH)—CH$_2$—group, wherein A' is a phenyl, a 2-fluorophenyl, a 3-chlorophenyl or a 3-trifluoromethylphenyl group, identical to A;

Z is lower alkyl, particularly methyl.

More particularly, advantageous active compounds, for use according to the present invention, are analogs of phenylethanolamines of formula I above, in which n is 1 or 2;

A is a phenyl, 3-chlorophenyl or 3-trifluoromethylphenyl group;

R' is a hydroxy group, carbomethoxy, carbethoxy carboxy, carbamoyl, carboxymethoxy, carbomethoxymethoxy or carbethoxymethoxy group;

R" and X are both hydrogen;

W is a direct bond;

Y is hydrogen or a A'—CH(OH)—CH$_2$—group wherein A', identical to A, is phenyl; and Z is methyl, particularly a N-[2-(4-carbomethoxyphenyl)-1-methylethyl]-2-hydroxy-2-phenylethylamine, or a N-[2-(4-carboxyphenyl)-1-methylethyl]-2-hydroxy-2-phenylethylamine, and their pharmaceutically acceptable salts. Particularly advantageous active compounds are N-[2-(4-carbomethoxyphenyl)-1-methylethyl]-2-hydroxy-2-phenylethylamine, hereinafter designated "Compound A", described in the Example 21 of European patent application 6735, in the form of the diastereoisomers mixture with a lower melting point, prepared as described in the "Description 15" of European patent application 21636; and its pharmaceutically acceptable salts, particularly the neutral fumarate;

N-[2-(4-carboxyphenyl)-1-methylethyl]-2-hydroxy-2-phenylethylamine, hereinafter designated "Compound B", prepared by saponification of Compound A, and its pharmaceutically acceptable salts;

(R,S)-N-(2-phenyl-2-hydroxyethyl)-1-methyl-3-(4-hydroxyphenyl)propylamine, hereinafter designated "Compound C", described in the Example 10 of U.S. Pat. No. 4,391,826; and its pharmaceutically acceptable salts, particularly the hydrochloride;

(R,S)-N-(2-phenyl-2-hydroxyethyl)-1-methyl-3-(4-aminocarbonylphenyl)propylamine, hereinafter designated "Compound D", described in the Example 15 of U.S. Pat. No. 4,391,826; and its pharmaceutically acceptable salts, particularly the hydrochloride;

p-[(R)-3-[bis-[(R)-beta-hydroxyphenethyl]amino]butyl]-benzamide, hereinafter designated "Compound E", described in the Example 12 of European patent application 101069, and its pharmaceutically acceptable salts, particularly the maleate and the fumarate;

p-[(S)-3-[bis-[(R)-beta-hydroxyphenethyl]amino]butyl]-benzamide, hereinafter designated "Compound F", described in the Example 8 of European patent application 101069; and its pharmaceutically acceptable salts;

(RR,SS)-N-[2-(4-carbomethoxyphenyl)-1-methylethyl]-2-hydroxy-2-(3-trifluoromethylphenyl)ethanamine, hereinafter designated "Compound G", described in the Example 19 of European patent application 40915, and its pharmaceutically acceptable salts, particularly hydrochloride;

(RR,SS)-N-[2-(4-carboxyphenyl)-1-methylethyl]-2-hydroxy-2-(3-trifluoromethylphenyl)ethanamine, hereinafter designated "Compound H", prepared by saponification of Compound G; and its pharmaceutically acceptable salts;

N-[2-(4-carbomethoxymethoxyphenyl)-1-methylethyl]-2-hydroxy-2-(3-chlorophenyl)ethanamine, hereinafter designated "Compound J", described in the Example 6 of European patent application 23385, and its pharmaceutically acceptable salts, particularly the hydrobromide, in its (RR,SS) form ("Description 21" of European patent application 70133); and N-[2-(4-carboxymethoxyphenyl)-1-methylethyl]-2-hydroxy-2-(3-chlorophenyl)ethanamine, hereinafter designated "Compound K", prepared by saponification of Compound J; and its pharmaceutically acceptable salts.

The compounds of formula I may be prepared as described in European published patent application Nos. 6735, 7204, 21636, 23385, 25331, 28105, 40000, 40915, 52963, 61907, 63004, 66351, 68669, 70133, 70134, 89154, 91749, 95827, 99707, 101069, 140359, 146392, 164700, 170121, 170135, 171519, in Belgian patent No. 900.983, in United Kingdom patent specification 2133986, in Australian published patent application 84/31944, in International published patent application WO 84/00956 and in U.S. Pat. No. 4,391,826.

BIOLOGICAL ACTIVITY

Rat Isolated Colon

Not fasted male rats, weighing 250–300 g are sacrificed. The proximal colon tract, consisting of a segment of about 2–3 cm, is removed and suspended in a 20 ml organs bath containing a Krebs-Ringer's solution having the following mM composition: NaCl 118.4; KCl 4.7; $CaCl_2$ 2.45; $MgSO_4$ 1.16; $NaH_2PO_4$ 3.7; Glucose 5.6; $NaHCO_3$ 30.9. The solution is gassed with a mixture of oxygen (95%) and $CO_2$ (5%) and its temperature is kept constant at 37° C. The colon segments, subjected to a traction of about 1 g, contract spontaneously. The compounds under evaluation are added after stabilisation of the preparation (2 h) and the minimal concentration that completely inhibits the rhythmical contractions of the preparation ($IC_{100}$) is determined.

The molar $IC_{100}$ of three representative active compounds of the present invention that inhibits the spontaneous motility of rat colon is indicated in Table I.

TABLE I

| Tested compound | $IC_{100}/M/$ |
|---|---|
| Compound A | $2.5 \cdot 10^{-7}$ |
| Compound B | $2.5 \cdot 10^{-6}$ |
| Compound C | $1 \cdot 10^{-6}$ |

Intestinal motility in anaesthetized rat

Male CD (Charles River, Italy) rats, weighing 300–350 g and having fasted for 18 hours are anaesthetized with ethylurethane (1.2 g/kg/5 ml, i.p.) and their corporeal temperature is kept uniform (37° C.±0.5) during the test. The motility is recorded with pressure microtransducers that are implanted on the proximal colonic section, 2–3 cm from the ileo-caecal junction. The microtransducers (0.8 cm×0.5 cm) are prepared according to the method described by X. B. Pascaud and al. (Am. J. Physiol. 1978, 235, E532-E538). The tested compounds are administered intravenously (femoral vein) (1 ml/kg) or intraduodenally (2 ml/kg) when the basal motility tracing was regular for 30 minutes at least. The electric signal corresponding to the mechanical activity of the colon is filtered (5 Hz) and recorded on a polygraph equipped with a computer for the subsequent data analysis. The parameters considered are the medium tonus and the energy coupled with the contraction (integrated electric signal).

Table II shows the minimal effective doses (MED) extrapolated from the log dose straight line in relationship with the considered value of the energy coupled with the contraction during a period of 10 minutes after the administration of the compounds.

TABLE II

| Active Compound | MED (mg/kg) | |
|---|---|---|
| | i.v. | i.d. |
| Compound A | 0.15 | 0.3 |
| Compound B | 0.07 | 0.4 |
| Compound C | 0.1 | 3.5 |

Gastrointestinal and colonic motility in dog

This study is carried out on adult dogs weighing 9–15 kg. The animals are equipped with pressure microtransducers implanted on the colon, 2, 8 and 12 cm from the ileo-caeco-colique valve. Some groups of electrodes are implanted on the stomach and on the small intestine:

Antrum (pylorus −5 cm)
Duodenal bulb (pylorus +5 cm) and/or duodenum (pylorus +12 cm)
Jejunum
Ileum A week after the operation, the gastric and intestinal electromyogram and the colonic mechanogram are recorded continuously. The direct registration of the electrical activity is obtained with a recorder type Alvar, with high speed of unrolling paper (1.5 cm/minute). The electrical activity is also derived on a potentiometer recorder with low speed of unrolling paper (6 cm/h) after quantifiying and summation during periods of 20 seconds. The recording of the colonic mechanogram is made on a potentiometer recorder. The colonic motility index, corresponding to the area determinated by the base line and the peaks curve of the contractions, is calculated, for periods of 20 minutes, with a computer system analysis using a microcomputer type Tandy TRS 80.

The compounds to be tested are administered either to the animal having fasted for 17 h or to the animal 2 h or 15 h after its meal, exactly at the beginning or at the end of the post-prandial motor response. In the case of tests with fasted animal, the administration is made either during the period of irregular activity of the migrating myoelectric complex (MMC) or during the rest period, 10 minutes after the regular phase of a complex.

(a) Motor gastrointestinal profile of reference

In dogs having fasted for 17 h, the electric rapid activity of the gut consists of spike bursts which superimpose upon the slow waves according to two modalities: in an aleatory way or overloading 30–70% of the slow waves (irregular activity) or systematically superimposing all the slow waves during 5–10 minutes (regular activity).

This activity shows a cyclic organization in migrating myoelectric complex: the phase of irregular activity (about 50–70 minutes) is followed by a phase of regular activity (5-10 minutes). A silent period follows this activity period for 20-30 minutes. These MMC appear about every 90-120 minutes.

The electric activity of the stomach is also organized in cycles: an active periode concomitant with the myoelectric complex of the jejunum (the maximum activity is found during the phase of regular activity) and a silent period lasting up to the phase of irregular activity of the following complex.

The ingestion of a standard meal causes immediately and for about 17 hours the disappearance of this both gastric and intestinal cyclic organization in favour of a permanent irregular activity. The reorganization in myoelectric complex starts at the distal portions of the small intestine.

(b) Motor colonic profile

The colonic mechanogram is characterized by potent and big amplitude contractions corresponding, on the electric plane, to spike bursts of a period of 7-10 seconds (LSB, Long Spike Burst). These contractions are assembled in short periods appearing every 20-40 minutes. Their frequency is higher on the proximal colon ($2.8\pm0.3$/h) than on the distal colon ($2.1\pm0.4$/h).

The ingestion of a meal causes an additional contraction on the whole colon corresponding to the gastro-colic reflex with an increase in the motility index on the proximal colon.

A period of hypomotility of about 60-70 minutes generally follows this immediate reply. Later on, an increase of colonic activity during 10-12 hours is observed with the increase of the frequency of the periods of colon contraction. The motility index is considerably redoubled.

(c) Effects of Compound A

The effects of Compound A on the small intestine of two fasted dogs treated with such compound, at the doses of 0.1, 0.2 and 1 mg/kg per os, are characterized by the lasting disappearance of the migrating myoelectric complexes, both on the duodenum and on the jejunum. The gastric activity is little influenced.

On the colon it is noted an inhibition of the motility shorter than that on the small intestine.

Toxicity

The compounds of formula I and their pharmaceutically acceptable salts are slightly toxic. Their acute toxicity is much lower than the estimed dose for a therapeutic treatment.

Particularly, some compounds of formula I have been described as potential therapeutic agents in the treatment of obesity (Nature, 1984, 309, 163-165) and one of them was tested in human clinical trials (Int. J. Obesity, 1985, 9, 230; ibid. 1985, 9, 231).

Thus, the present invention relates to a method for the treatment and/or prophylaxis of the gastrointestinal diseases in mammals, which comprises administering a prophylactic and/or effective amount of a compound of formula I or of one of its pharmaceutically acceptable salts to said mammals in need of such prophylaxis and/or treatment.

The diseases that may be treated with the compounds of formula I hereinabove particularly include those being due to the contractions of smooth muscle, more particularly irritable bowel syndrome and spasms accompanying the peptic ulcer.

The compounds of formula I hereinabove may be administered, according to the present invention, in the daily dose of from 0.01 to 10 mg per kg of body weight of the mammal to be treated, preferably in a daily dose of from 0.1 to 5 mg/kg. In human beings the daily dose may preferably vary from 0.5 mg to 500 mg, more particularly from 2.5 to 250 mg according to the age of the treated subject, to the type of treatment i.e., prophylactic or curative, and to the severity of the affection or of the gastrointestinal disease. The compounds of formula I are generally administered in unit dose form of from 0.1 to 100 mg, preferably of from 0.5 to 50 mg of active ingredient, 1 to 5 times daily.

Said unit doses are preferably formulated in pharmaceutical compositions in which the active compound of formula I is in admixture with a pharmaceutical carrier.

Therefore, the active compounds of formula I above and their pharmaceutically acceptable salts are used for the preparation of pharmaceutical compositions for the prophylaxis and/or the treatment of gastro-intestinal diseases associated with a smooth muscle contraction.

Thus, it is another object of the present invention to provide pharmaceutical compositions useful for the treatment of gastrointestinal diseases associated with a contraction of the smooth muscle, said compositions containing a compound of formula I hereinabove or one of its pharmaceutically acceptable salts as active ingredients.

In the pharmaceutical compositions of the present invention the active ingredient of formula I may be administrered by oral, sublingual, subcutaneous, intramuscular, intravenous, transdermical or rectal route in unit forms of administration, in admixture with conventional pharmaceutical carriers, to animals and human beings. Appropriate unit forms of administration include tablets, capsules, powders, granules and oral solutions or suspensions and forms for sublingual and buccal administration, forms for intramuscular and intravenous administration as well as forms for rectal administration.

The compositions of the present invention may contain the unit dose of the active compound indicated hereinabove in admixture with the pharmaceutical carrier and may be administered from 1 to 5 times per day as indicated hereinabove.

When a solid composition is prepared in tablet form, the main active ingredient is mixed with a pharmaceutical carrier such as gelatine, starch, lactose, magnesium stearate, talc, arabic gum and the like. Tablets may be coated with sucrose or other suitable materials or they may be treated so that their activity is extended or delayed and that they continually release a predetermined amount of active ingredient.

A preparation in capsules is obtained by mixing the active ingredient with a diluent and a lubricant and by pouring the mixture thus obtained in soft or hard capsules.

A liquid preparation in the form of syrup or elixir or for the administration in drops may contain the active ingredient jointly with a possibly acaloric sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents.

For rectal administration, suppositories are prepared with binding agents melting at rectal temperature, for example, cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules or microemulsions, possibly with one or more supports or additives.

The compositions of the present invention may contain, beside the compounds of formula I hereinabove or one of their pharmaceutically acceptable salts, other active ingredients such as, for example, analgesics, tranquillizers or other drugs useful in the treatment of intestinal diseases.

The following examples illustrate the invention without however limiting it.

PREPARATION 1

Compound A.

(a) A mixture of 9 g of 2-amino-1-phenylethanol and 12.7 g of 4-carbomethoxyphenylacetone is refluxed for one hour in 150 ml of absolute ethanol. After cooling, 1 g of palladium on carbon is added. The reaction mixture is hydrogenated under 4.053 bar for 5 hours at 60° C. Then it is filtered, evaporated to dryness, the residue is taken up with a mixture of 40 ml of methanol and 40 ml of ethyl ether and the solution is kept for 48 hours at 0°-4° C. After crystallization and filtration, 5.5 g of N-[2-(4-carbomethoxyphenyl)-1-methylethyl]-2-hydroxy-2-phenylethylamine are obtained; m.p. 120°-125° C. (by recrystallization from methanol, 4.4 g of pure product, mixture of isomers with a higher melting point, are obtained; m.p. 126°-128° C.).

(b) The mother-liquors of crystallization, obtained in step (a) are evaporated to dryness and the crude oil (13 g) so obtained is dissolved in a mixture of 15 ml of ethyl ether and 30 ml of n-hexane. The crystalline solid which forms (9 g) melts at 81°-84° C. To a solution of this solid in 30 ml of warm ethanol 100 ml of warm water are added at 80° C. to obtain an oil which crystallizes and is recovered by filtration. Thus 7.2 g of N-[2-(4-carbomethoxyphenyl)-1-methylethyl]-2-hydroxy-2-phenylethylamine, mixture of isomers with lower melting point, are obtained; m.p. 84°-86° C. (Compound A). By adding an aqueous solution of 0.01 moles of fumaric acid to 0.02 mole of the base, the neutral fumarate of Compound A is obtained.

PREPARATION 2

Compound B.

A mixture of 9.2 g of sodium hydroxide, 60 ml of water, 60 ml of ethanol and 7.2 g of Compound A is refluxed for one hour, then the ethanol is evaporated, the aqueous phase is filtered and made acid to pH 5 with hydrochloric acid. The gel so obtained is separated by decantation and dissolved in ethanol. The solvent is evaporated to dryness and the residue is taken up with warm ethanol and filtered. By addition of isopropanol and crystallization, 1.5 g of N-[2-(4-carboxyphenyl)-1-methylethyl]-2-hydroxy-2-phenylethylamine, mixture of isomers with lower melting point are obtained; m.p. 170°-172° C. (Compound B).

By operating as described above, starting from the isomer of higher melting point of the PREPARATION 1 (a), N-[2-(4-carboxyphenyl)-1-methylethyl]-2-hydroxy-2-phenylethylamine, mixture of isomers with higher melting point which crystallizes from methanol, is obtained; m.p. 205°-207° C.

PREPARATION 3

Compound H.

Starting from Compound G, by operating as described in PREPARATION 2, (RR,SS)-N-[2-(4-carboxyphenyl)-1-methylethyl]-2-hydroxy-2-(3-trifluoromethylphenyl)ethanamine is obtained (Compound H).

PREPARATION 4

Compound K.

Starting from Compound J, by operating as described in PREPARATION 2, N-[2-(4-carboxymethoxyphenyl)-1-methylethyl]-2-hydroxy-2-(3-chlorophenyl)-ethanamine is obtained (Compound K).

EXAMPLE 1.

Capsules comprising one of the active ingredients of formula I, having the following composition:

| Compound A (as neutral fumarate) | 17.5 mg |
|---|---|
| lactose | 120.0 mg |
| magnesium stearate | 5.0 mg | are prepared by mixing intimately charges of the above ingredients and introducing the mixture into hard gelatine capsules. These capsules contain 15 mg of free base active ingredient.

EXAMPLE 2.

Tablets comprising one of the active ingredients of formula I, having the following composition:

| Compound B | 20 mg |
|---|---|
| lactose | 100 mg |
| microcrystalline cellulose | 30 mg |
| dried corn starch | 40 mg |
| magnesium stearate | 5 mg | are prepared by crushing the active ingredient to a particle dimension of 0.4 mm size, by passing it through a 0.4 mm sieve, by mixing the crushed mixture with the other constituents and compressing to form the tablets. In the same manner, tablets containing 40 mg of active ingredient are prepared.

EXAMPLE 3.

By operating as described in Example 2 hereinabove, tablets having the following composition are prepared:

| Compound A (as neutral fumarate) | 58.3 mg |
|---|---|
| lactose | 95.0 mg |
| dried corn starch | 100.0 mg |
| talc | 4.5 mg |

These tablets contain 50 mg of free base active ingredient.

EXAMPLE 4.

10,000 capsules containing 50 mg of free base active ingredient, are prepared from the following constituents: 583 g of neutral fumarate of Compound A, 495 g of microcrystalline cellulose, 5 g of amorphous silica gel. The above components are well mixed and introduced into hard gelatin capsules of dimension 4.

EXAMPLE 5.

A sterile aqueous solution useful for parenteral use containing one of the active ingredients of formula I, having the following composition:

| Compound G (as hydrochloride) | 32.8 mg |
|---|---|
| sodium chloride | 5.0 ml |
| distilled water to | 2.0 ml | is prepared. Each ampoule contain 30 mg of free base active ingredient.

EXAMPLE 6.

Suppositories comprising one of the active compounds of formula I, having the following composition:

| Compound G | 50 mg |
|---|---|
| lactose | 250 mg |
| Witespol W 45 to | 1.7 mg |

The active substance is mixed with the lactose and the mixture is placed uniformly in suspension in the molten mass for suppositories. The suspension is poured into cooled moulds to form suppositories weighing 1.7 g.

EXAMPLE 7.

Tablets comprising one of the active ingredients of formula I, having the following composition:

| Compound J (as hydrobromide) | 30.8 mg |
|---|---|
| lactose | 95.0 mg |
| dried corn starch | 45.0 mg |
| colloidal silica | 2.0 mg |
| soluble starch | 5.0 mg |
| magnesium stearate | 3.0 mg | are prepared by mixing the active substance with a part of the adjuvants. The mixture is granulated with a solution of soluble starch in water. After the granulate is dried, the remaining adjuvants are added and the tablets are made by compression. The tablets thus obtained contain 25 mg of free base active substance.

What is claimed is:

1. A method for treatment of gastrointestinal disease associated with smooth muscle contraction, comprising the step of administering to a mammal, in need of treatment of a gastrointestinal disorder or disease associated with smooth muscle contraction, an effective therapeutic amount of a phenylethanolamine analog having the formula

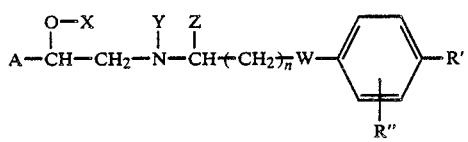

wherein:

$n$ is 1, 2 or 3;

A is a benzofuran-2-yl group or a phenyl group unsubstituted or substituted with one or two halogen atoms, a lower alkyl or a trifluoromethyl group;

R' is hydrogen; a lower alkyl group; a functional group selected from the group consisting of: hydroxy; lower alkoxy; lower alkenyloxy; lower alkynyloxy; cycloalkyloxy; lower cycloalkyl-alkoxy; benzyloxy; phenoxy; mercapto; (lower alkyl)thio; (lower alkenyl)thio; (lower alkynyl)thio; cycloalkylthio; (cycloalkyl-lower alkyl)thio; benzylthio; phenylthio; (lower alkyl)sulfinyl; (lower alkenyl)sulfinyl; (lower alkynyl)sulfinyl; cycloalkylsulfinyl; (cycloalkyl-lower alkyl)sulfinyl; benzylsulfinyl; phenylsulfinyl; (lower alkyl)sulfonyl; (lower-alkenyl)sulfonyl; (lower alkynyl)sulfonyl; cycloalkylsulfonyl; (cycloalkyl-lower alkyl)sulfonyl; benzylsulfonyl; phenylsulfonyl; cyano; nitro; amino unsubstituted or substituted with one or two identical or different radicals selected from the group consisting of lower alkyl, lower alkenyl, lower alkynyl, cycloalkyl, cycloalkyl-lower alkyl, benzyl, phenyl; carboxy; lower carbalkoxy; (lower alkenyloxy)carbonyl; (lower alkynyloxy)carbonyl; cycloalkyloxycarbonyl; (cycloalkyl-lower alkoxy)carbonyl; benzyloxycarbonyl; phenoxycarbonyl; carbamoyl unsubstituted or substituted on the amino group with one or two identical or different radicals, selected from lower alkyl, lower alkenyl, lower alkynyl, cycloalkyl, cycloalkyl-lower alkyl, benzyl, phenyl; a radical R selected from the group consisting of a lower alkyl group substituted with a functional group, a lower alkenyl group substituted with a functional group, a lower alkynyl group substituted with a functional group, a (lower alkyl)phenyl group substituted on the benzene ring with a lower alkyl or a functional group, a (lower alkenyl)phenyl group substituted on the phenyl ring with a lower alkyl or a functional group, a (lower alkynyl)phenyl group substituted on the benzene ring with a lower alkyl or a functional group, a benzyl group substituted on the benzene ring with a lower alkyl or a functional group, or a phenyl group unsubstituted or substituted with a lower alkyl or a functional group, the functional group being as defined hereinabove; an O-R group, wherein R is as defined hereinabove; an S-R group, wherein R is as defined hereinabove; an SO-R group, wherein R is as defined hereinabove; an $SO_2$-R group, wherein R is as defined hereinabove; an NRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine; a COOR group, wherein R is as defined hereinabove; a CO-SR group, wherein R is as defined hereinabove; a CONRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine; an $SO_2NRR°$ group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine;

R" represents hydrogen; a halogen; a lower alkyl; a functional group as defined hereinabove; an O-R group, wherein R is as defined hereinabove; a COOR group, wherein R is as defined hereinabove; a CONRR° group, wherein R is as defined hereinabove and R° represents hydrogen or has the meaning as defined hereinabove for R, or R and R° form, together with the nitrogen atom to which they are bound, a ring selected from the group consisting of pyrrolidine, piperidine and morpholine W represents a direct bond or an oxygen atom;

X represents hydrogen, a lower alkyl or a lower alkanoyl;

Y represents hydrogen, or an A'—CH(OH)—CH$_2$—group, wherein A' is identical to A, but other than benzofuran-2-yl; or X and Y, together, form a methylene group, unsubstituted or substituted with a lower carbalkoxy group; an ethylene group, unsubstituted or substituted with an oxo group; or a 1,3-propylene group; and Z represents hydrogen or a lower alkyl; or a pharmaceutically acceptable salt thereof.

2. A method according to claim 1, wherein said phenylethanolamine analog has formula I wherein:
n is 1 or 2;
A is a phenyl, 2-fluorophenyl, 3-chlorophenyl or 3-trifluoromethylphenyl;
R' is a functional group selected from the group consisting of hydroxy, lower carbalkoxy, carboxy, carbamoyl; or a O-R group, wherein R is a lower alkyl group or a lower alkenyl substituted with a functional group selected from lower carbalkoxy and carboxy;
R" and X are both hydrogen;
W is a direct bond;
Y is hydrogen or a A'—CH(OH)—CH$_2$—group, wherein A' is a phenyl, a 2-fluorophenyl, a 3-chlorophenyl or a 3-trifluoromethylphenyl group, identical to A;
Z is a lower alkyl.

3. A method according to claim 1, wherein said phenylethanolamine analog has formula I wherein:
n is 1 or 2;
A is a phenyl, 3-chlorophenyl or 3-trifluoromethylphenyl group;
R' is a hydroxy group, carbomethoxy, carbethoxy, carboxy, carbamoyl, carboxymethoxy, carbomethoxymethoxy or carbethoxymethoxy group;
R" and X are both hydrogen;
W is a direct bond;
Y is hydrogen or a A'—CH(OH)—CH$_2$—group wherein A', identical to A, is phenyl; and
Z is methyl.

4. A method according to claim 1, wherein said phenylethanolamine analog is N-[2-(4-carbomethoxyphenyl)-1-methylethyl]-2-hydroxy-2-phenylethylamine or a pharmaceutically acceptable addition salt thereof.

5. A method according to claim 1, wherein said phenylethanolamine analog is the neutral fumarate of N-[2-(4-carbomethoxyphenyl)-1-methylethyl]-2-hydroxy-2-phenylethylamine in mixture of diastereoisomers with lower melting point.

6. A method according to claim 1, wherein said phenylethanolamine analog is N-[2-(4-carboxyphenyl)-1-methylethyl]-2-hydroxy-2-phenylethylamine or a pharmaceutically acceptable salt thereof.

7. A method according to claim 1, wherein said phenylethanolamine analog is (R,S)-N-(2-phenyl-2-hydroxyethyl)-1-methyl-3-(4-hydroxyphenyl)-propylamine or a pharmaceutically acceptable salt thereof.

8. A method according to claim 1, wherein said phenylethanolamine analog is (R,S)-N-(2-phenyl-2-hydroxyethyl)-1-methyl-3-(4-aminocarbonylphenyl)-propylamine or a pharmaceutically acceptable salt thereof.

9. A method according to claim 1, wherein said phenylethanolamine analog is p-[(R)-3-[bis-[(R)-beta-hydroxyphenethyl]amino]butyl]-benzamide or a pharmaceutically acceptable salt thereof.

10. A method according to claim 1, wherein said phenylethanolamine analog is (RR,SS)-N-[2-(4-carbomethoxyphenyl)-1-methylethyl]-2-hydroxy-2-(3-trifluoromethylphenyl)ethanamine or a pharmaceutically acceptable salt thereof.

11. A method according to claim 1, wherein said phenylethanolamine analog is (RR,SS)-N-[2-(4-carboxyphenyl)-1-methylethyl]-2-hydroxy-2-(3-trifluoromethylphenyl)ethanamine or a pharmaceutically acceptable salt thereof.

12. A method according to claim 1, wherein said phenylethanolamine analog is N-[2-(4-carbomethoxymethoxyphenyl)-1-methylethyl]-2-hydroxy-2-(3-chlorophenyl)ethanamine or a pharmaceutically acceptable salt thereof.

13. A method according to claim 1, wherein said phenylethanolamine analog is (RR,SS)-N-[2-(4-carbomethoxymethoxyphenyl)-1-methylethyl]-2-hydroxy-2-(3-chlorophenyl)ethanamine or its hydrobromide.

14. A method according to claim 1, wherein said phenylethanolamine analog is N-[2-(4-carboxymethoxyphenyl)-1-methylethyl]-2-hydroxy-2-(3-chlorophenyl)ethanamine or a pharmaceutically acceptable salt thereof.

15. A method according to claim 1, wherein said effective amount of said phenylethanolamine analog is a daily dose of 0.01 to 10 mg per kg of body weight of the treated mammal.

16. A method according to claim 1, wherein said mammal is a human and said effective amount of said phenylethanolamine analog is a daily dose of from 0.5 to 500 mg.

17. A method according to claim 1, wherein said phenylethanolamine analog is administered in unit doses containing from 0.1 to 100 mg thereof.

18. A method according to claim 15, wherein said daily dose is 0.1 to 5 mg per kg of body weight of the treated mammal.

19. A method according to claim 16, wherein said daily dose is 2.5 to 250 mg.

20. A method according to claim 17, wherein said unit doses contain from 0.5 to 50 mg of said phenylethanolamine analog.

21. A method according to claim 1, wherein said gastrointestinal disease is irritable bowel syndrome or peptic ulcer spasms.

* * * * *